United States Patent [19]

Miyaki et al.

[11] Patent Number: 4,794,088
[45] Date of Patent: Dec. 27, 1988

[54] METHOD AND APPARATUS FOR SEPARATING AND ANALYZING USING LIQUID CHROMATOGRAPHY

[75] Inventors: Yoshiyuki Miyaki; Toshiya Kataoka, both of Shin-nanyo, Japan

[73] Assignee: Toyo Soda Manufacturing Co., Ltd., Shin-nanyo, Japan

[21] Appl. No.: 908,793

[22] Filed: Sep. 18, 1986

[30] Foreign Application Priority Data

Sep. 25, 1985 [JP] Japan .................. 60-210074

[51] Int. Cl.$^4$ .................. G01N 30/02; G01N 30.84
[52] U.S. Cl. .................. 436/161; 73/61.1 C; 210/198.2; 210/321.6; 210/321.72; 210/321.74; 210/656; 210/500.21; 210/500.23; 422/70; 436/178
[58] Field of Search .................. 422/68, 69, 70; 436/161, 178; 210/198.2, 321.1, 321.2, 649, 656, 659, 500.21, 500.23, 321.6, 321.72, 321.74; 73/61.1 C

[56] References Cited

U.S. PATENT DOCUMENTS

| | | | |
|---|---|---|---|
| 3,399,972 | 9/1968 | Skeggs et al. .................. | 422/70 X |
| 3,425,562 | 2/1969 | Hamer .................. | 210/321.1 |
| 3,442,389 | 5/1969 | Mendelson .................. | 210/321.2 |
| 3,450,508 | 6/1969 | Cooper et al. .................. | 210/321.2 X |
| 3,495,943 | 2/1970 | Kapff .................. | 210/321.2 X |
| 3,541,006 | 11/1970 | Bixler et al. .................. | 210/321.1 X |
| 3,834,546 | 9/1974 | Brun et al. .................. | 210/321.1 |
| 4,075,100 | 2/1978 | Furuta et al. .................. | 210/321.2 X |
| 4,262,041 | 4/1981 | Eguchi et al. .................. | 210/500.34 X |
| 4,365,023 | 12/1982 | Fujimoto et al. . | |
| 4,477,596 | 10/1984 | Fujimoto . | |
| 4,514,304 | 4/1985 | Miyaki et al. .................. | 210/500.41 X |
| 4,554,376 | 11/1985 | Fujimoto et al. .................. | 562/554 |

FOREIGN PATENT DOCUMENTS 0032770 7/1981 European Pat. Off. .
0075371 3/1983 European Pat. Off. .

OTHER PUBLICATIONS

Machleidt et al, Z. Anal. Chem., vol. 252, pp. 151-158, 1970.
Science, vol. 224, pp. 74-76 (Apr. 6, 1984), Fujimoto et al.

Primary Examiner—Barry S. Richman
Assistant Examiner—Robert J. Hill, Jr.
Attorney, Agent, or Firm—Oblon, Fisher, Spivak, McClelland & Maier

[57] ABSTRACT

A method and apparatus for separating and analyzing using liquid chromatography, wherein an eluate from a chromatographic column is treated by dialysis using an amphoteric ion exchange membrane.

20 Claims, 2 Drawing Sheets

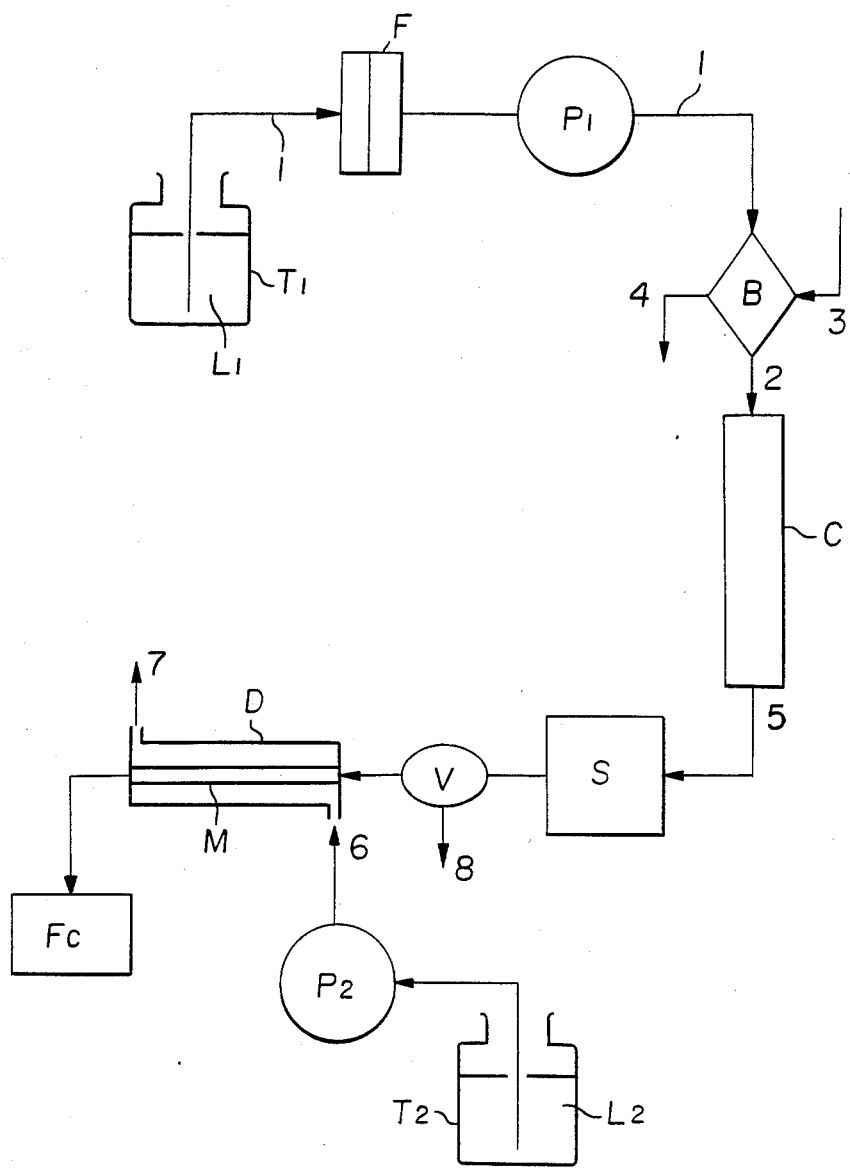

METHOD AND APPARATUS FOR SEPARATING AND ANALYZING USING LIQUID CHROMATOGRAPHY

BACKGROUND OF THE INVENTION

1. Field of the Invention

The present invention relates to a method and apparatus for the separation and analysis by liquid chromatography. More particularly, it relates to a method and apparatus for the separation and analysis by liquid chromatography, whereby a variety of substances can be separated and purified quickly and highly efficiently, and can be analyzed with high sensitivity.

2. Description of the Related Art

In recent years, there has been a rapid progress in the techniques for the separation and analysis by liquid chromatography, and it has been made possible to separate various substances ranging from low molecular weight to high molecular weight substances. However, in general, in aqueous liquid chromatography, the eluting solution (mobile phase) contains various salts in high concentrations depending upon the sample to be eluted. Therefore, there have been problems such that in the analysis of the eluted sample, the detection by an electric conductance meter, an ultraviolet absorption meter or a differential refractometer is difficult, and that in the fractionation of the sample into the individual components, desalination of the eluted sample is problematic. For the desalination of such a sample, it is conceivable to employ diffusion dialysis by means of a cellulose-type dialysis membrane, ultrafiltration by means of an ultrafilter and electrodialysis. However, in the diffusion dialysis or in the ultrafiltration, leakage of a sample having a molecular weight of 5000 or less is substantial, and no adequate desalination can be accomplished. On the other hand, in the electrodialysis, the apparatus is complex and large-sized, and as such, it is not suitable for application to chromatography. Besides, it is difficult to thereby accomplish the desalination to a low salt concentration (a few hundreds ppm or less). Further, in the separation by liquid chromatography, it becomes necessary to introduce a certain electrolyte to the column eluate, for instance, for the exchange of the buffer solution after the elution from the column for the stabilization of the sample. In such a case, the conventional methods have the same difficulties as mentioned above when the molecular weight of the sample is low.

In liquid chromatography, particularly in ion chromatography, it has been proposed to improve the analytical sensitivity by treating the eluate from the column by a membrane (e.g. Japanese Unexamined Patent Publication No. 66052/1983 and European Pat. No. 32770). However, in this case, a cation exchange membrane is used between the column eluate and the regenerant. Therefore, although the cation exchange is adequately conducted, other ionic impurities contained in the column eluate can not be removed, and no adequate improvement in the sensitivity is accomplished. Further, it is thereby difficult to introduce the necessary electrolyte to the column eluate.

SUMMARY OF THE INVENTION

It is an object of the present invention to solve the above-mentioned problems inherent to the conventional aqueous liquid chromatography, and to provide a method and apparatus whereby precise separation and precise analysis of various substances can be simply and highly efficiently conducted with a high sensitivity.

The present invention provides a method for the separation and analysis by liquid chromatography, wherein an eluate from a chromatographic column is treated by dialysis by means of an amphoteric ion exchange membrane. Further, the present invention provides an apparatus for the separation and analysis by liquid chromatography, which is provided with an amphoteric ion exchange membrane dialyzer for a chromatographic eluate.

BRIEF DESCRIPTION OF THE DRAWINGS

FIGS. 1 and 2 illustrate preferred embodiments of the present invention, where like reference numerals indicate like parts.

DETAILED DESCRIPTION OF THE PREFERRED EMBODIMENTS

Figure 1:
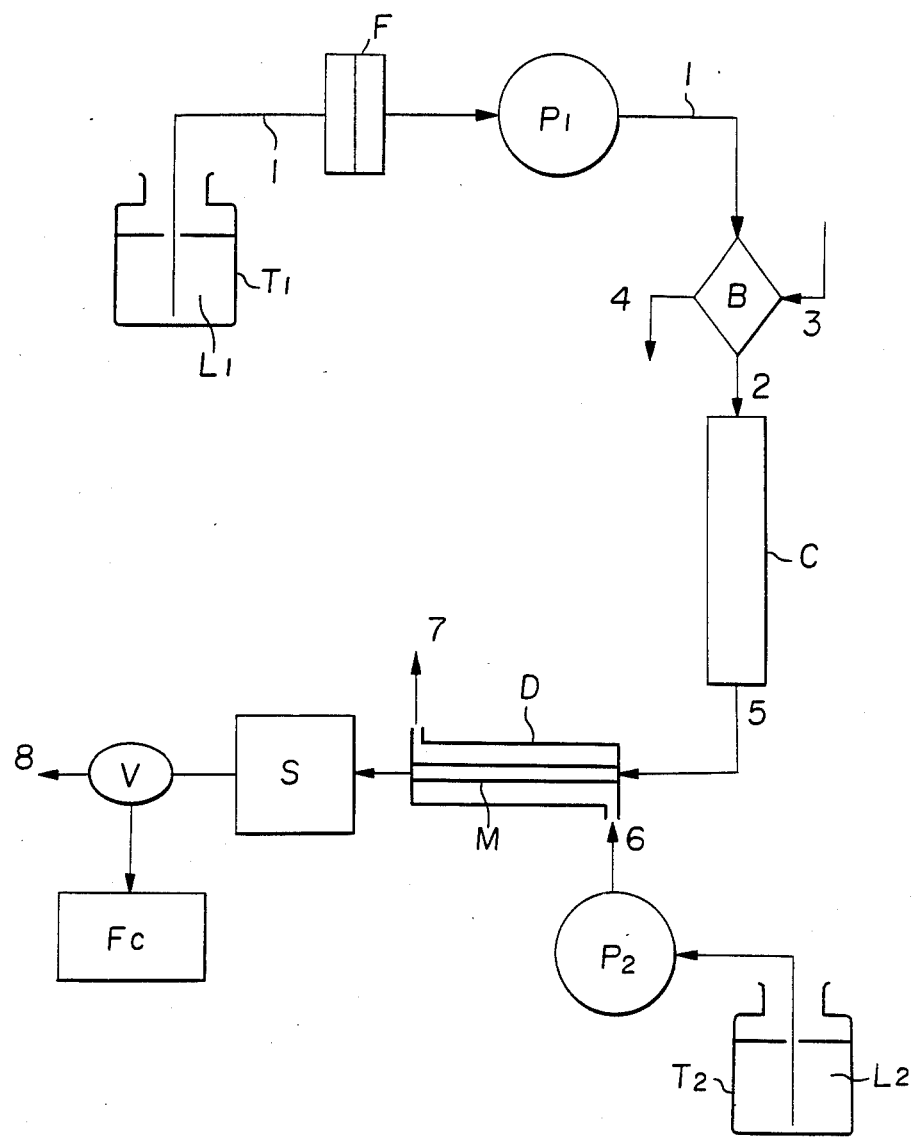

The present invention is concerned with a method for the fractionation and analysis by liquid chromatography, which is characterized in that the eluate of the liquid chromatography is treated by dialysis by means of an amphoteric ion exchange membrane, and with an apparatus for the separation and analyss by liquid chromatography, which is characterized in that a dialyzer made of an amphoteric ion exchange membrane is provided as a post column treating device.

In the present invention, the amphoteric ion exchange membrane is a membrane comprising cation exchange regions and anion exchange regions, or comprising these two regions and regions having no ion exchagge groups. The cation exchage regions are regions having functional groups which provide a fixed negative charge when ionized, such as carboxylic acid groups or sulfonic acid groups. Whereas, the anion exchange regions are regions having functional groups which provide a fixed positive charge when ionized, such as primary, secondary, tertiary or quaternary ammonium groups. These cation exchange regions and anion exchange regions are preferably arranged alternately, and the distance between the respective centers of the adjacent regions, is usually at most 1 mm, preferably at most 0.1 mm. The cation and anion exchange capacities are usually from 0.1 to 2 meq/g dry resin, preferably from 0.3 to 2 meq/g dry resin. When the amphoteric ion exchange membrane does not satisfy these conditions, the effects obtainable by the present invention will be substantially impaired. The amphoteric ion exchange membane to be used in the present invention is required to satisfy the following conditions in addition to the above.

(i) When an aqueous potassium chloride solution of 0.02 mol/liter and an aqueous potassium chloride solution of 0.01 mol/liter are partitioned by the membrane, the potential difference as measured between both sides of the membrane is within a range of from $-8$ to $+8$ mV, preferably from $-4$ to $+4$ mV.

(ii) The membrane resistance as measured in 0.5 mol/liter of an aqueous potassium chloride solution is at most 50 ohm.cm$^2$, preferably at most 20 ohm.cm$^2$. If the amphoteric ion exchange membrane does not satisfy these conditions, the permeability of the membrane to the electrolyte is low, whereby the effects of the present invention tend to be impaired.

The above-mentioned amphoteric ion exchange membrane used in the present invention, may be prepared by various methods. A method for the preparation is described in detail, for instance, in "Membranes" Vol. 8, No. 4, p 212–224 (1983). In one example, a polymer, poly A, into which cation exchange groups can be introduced, a polymer, poly B, into which anion exchange groups can be introduced, and if necessary, a polymer, pol C, into which no ion exchange groups can be introduced, are blended, and formed into a membrane having a desired shape, and then the cation and anion exchange groups are introduced. Further, if necessary, the membrane is further sujected to cross-linking. Otherwise, anion exchange groups are introduced to a film prepared by a blend of a polymer, poly $A^+$, having cation exchange groups and a polymer, poly B, into which anion exchange groups can be introduced. Likewise, cation exchange groups are introduced to a film prepared by a blend of a polymer, poly A, into which cation exchange groups can be introduced and a polymer, poly $B^-$, having anion exchange groups. When these polymers are blended, a polymer, poly C, into which no ion exchange groups can be introduced, may further be incorporated, as the case requires. Otherwise, monomers into which no ion exchange groups can be introduced, are preliminarily copolymerized with poly A, poly $A^+$, poly B and poly $B^-$ (to form any one of random, alternating and block copolymers), and the copolymers thereby obtained are blended. Also in this case, cross-linking may be conducted as the case requires. As another method, a block copolymerization method may be mentioned. For instance, a block copolymer wherein poly A into which cation exchange groups can be introduced, poly B into which anion exchange groups can be introduced, and, if necessary, poly C into which no ion exchange groups can be introduced, are linked in a straight chain, is prepared by block copolymerization; then, a membrane having a desired shape is prepared from the block copolymer; and thereafter cation groups and anion groups are introduced into poly A and poly B, respectively.

As specific examples of the block copolymer, there may be mentioned linearly linked copolymers such as (poly A-poly B)$_n$, pol A-poly B-poly A, poly B-poly A-poly B, poly A-poly C-poly B, poly A-poly C-poly B-poly C, poly C-poly A-poly C-poly B, poly C-poly A-poly C-poly B, poly A-poly C-poly B-poly C-poly A and poly B-poly C-poly A-poly C-poly B. However, a copolymer having poly C between poly A and poly B is preferred. Further, a graft block copolymer may also be used. For instance, an amphoteric ion exchange membrane may be obtained by preparing a graft block copolymer having a variety of combination such as poly B having poly A as its branches, poly A having poly B as its branches, poly B having a (poly A-poly C)$_n$ block copolymer as its branches, poly A having a (poly B-poly C)$_n$ block copolymer as its branches, poly A having a poly C-poly B-poly C block copolymer as its branches, poly Bhhaving a poly C-poly A-poly C block copolymer as its branches, or poly C having poly A and poly B as its branches; then, forming tne graft block copolymer into a membrane; and introducing the respective ion exchange groups. In each case, cross-linking may be conducted depending upon the particular purpose.

With respect to the materials used for the preparation of the amphoteric ion exchange membrane, poly A into which cation exchange groups can be introduced, includes polymers of monomers having an aromatic ring which can be readily be sulfonated by a known method, such as styrene, α-methylstryene, vinyl toluene, vinyl naphthalene, α-halogenostyrene, diphenylbutadiene, o-, m- or p-chlorostyrene, o-, m- or p-hydroxystyrene, and o-, m- or p-hydroxystyrene derivative (e.g. o-, m- or p-methoxystyrene, o-, m- or p-acetoxystyrene, or o-, m- or p-tert-butoxystyrene), and polymers of monomers into which carboxylic acid groups can readily be introduced by hydrolysis, for example, unsaturated carboxylates such as acrylates, methacrylates, crotonates and conjugated diene carboxylates; monomers having a cyano group such as acrylonitrile, methacrylonitrile or vinylidene cyanide; alkylidene malonates; or α-cyanoacrylates. Poly B into which anion exchange groups can be introduced, includes polymers of vinylpyridines, vinylpyrimidines, vinyl quinolines, vinyl carbazoles, and o-, m- or p-vinylphenylalkylene dialkylamines of the formula:

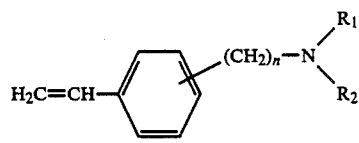

wherein n is an integer of from 1 to 3, and each of $R_1$ and $R_2$ is an alkyl group having from 1 to 12 carbon atoms. These polymers can readily be quaternized with an alkyl halide compound. Further, poly C into which no ion exchange groups can be introduced, includes polymers of dienes such as butadiene, isoprene, pentadiene and cyclohexadiene. These polymers can readily be cross-linked by a known method. When no sulfonization is required in the process for the preparation of the amphoteric ion exchange membrane, poly C may be polymers of aromatic monomers such as styrene, vinyl toluene, α-methylstyrene and vinyl xylene.

The above-mentioned blend or block copolymer preferably contains at least 15% by weight of each of poly A into which cation exchange groups can be introduced and poly B into which anion exchange groups can be introduced, and the molecular weights of the constituting polymers are preferably from $10^3$ to $10^6$ g/mol.

In the method for the fractionation and analysis by liquid chromatography according to the present invention, a sample is introduced into a chromatographic column by means of a suitable injection valve; an eluting solution (mobile phase) is permitted to flow through the column to chromatographically completely or partially separate sample bands; the eluate from the column is sent to a flow passage formed by the amphoteric ion exchange membrane; chromatographic peaks are detected prior to or after the introduction, by means of a suitable detector (such as an infrared absorption photometer, a variety of electrochemical detecting devices, an electric conductance meter, an ultraviolet absorption meter, a differential refractometer or light scattering photometer); and finally, samples of the respective fractions are recovered. In the flow passage formed by the amphoteric ion exchange membrane, the eluate from the column flows in contact with one side of hhe amphoteric ion exchange membrane, while a dialyzate solution is permitted to flow at the other side of the membrane so that a low molecular weight electrolyte in the column eluate diffuses through the membrane to the dialytic solution side, or a low molecular weight electrolyte diffuses from the dialyzate solution side through the membrane to the column eluate side. By the use of the amphoteric ion exchange membrane, it is possible not only to increase the diffusion rate of a low molecular weight electrolyte through the membrane, but also to improve the selectivity between an electrolyte and a non-electrolyte in the permeability of the membrane over the conventional dialysis membranes, whereby it is possible to conduct an ideal post column treatment with a minimum loss of the sample. Further, by using pure water or an aqueous solution containing an electrolyte having a molar concentration lower than the molar concentration of the electrolyte in the column eluate, as the dialyzate solution, it is possible to remove a low molecular weight electrolyte contained in the column eluate, whereby the analytical precision can be improved. This effectiveness is greater as the concentration of the electrolyte in the dialyzate solution is lower. The dialyzate solution may contain at least $10^4$ g/mol of non-electrolytes, for example, saccharides such as glucose, saccharose and raffinose, oligosaccharide, alcohols, polyols, ethers, polyethers, ketones or acetonitriles, in a concentration of not higher than 50 g/dl. The amphoteric ion exchange membrane has a low permeability to a non-electrolyte, and the osmotic pressure created by this non-electrolyte serves to facilitate the diffusion of an electrolyte from the column eluate through the the amphoteric ion exchange membrane to the dialyzate solution. However, if the non-electrolyte is of a low molecular weight at a level of $10^2$ g/mol or less, such a non-electrolyte tends to diffuse through the amphoteric ion exchange membrane to the column eluate side in a substantial amount and interfere with the separation and purification or the analysis by chromatography, whereby the analytical sensitivity will be impaired.

When a necessary low molecular weight electrolyte is to be introduced from outside to the column eluate in the dialytic treatment, the electrolyte to be introduced may be incorporated to the dialyzate solution in a necessary concentration. The same will apply to the case where the electrolyte in the column eluate is to be exchanged. In order to conduct the exchange more efficiently, the dialysis by the amphoteric ion exchange membrane may be conducted in two steps in such a manner that in the dialysis of the first step, a low molecular weight electrolyte is removed from the column eluate by using a dialyzate solution prepared in the above-mentioned manner, and then, in the dialysis of the second step, the necessary electrolyte is introduced to the column eluate by using a dialytic solution containing the electrolyte.

The flow passage formed by the amphoteric ion exchange membrane is required to have a small width and a large surface area of the membrane in contact with the column eluate in order to minimize the spread of the sample bands and to effectively conduct the removal or exchange of the electrolyte in the column eluate or the introduction of an electrolyte to the column eluate. In the present invention, the flow passage formed by the amphoteric ion exchange membrane, preferably has a cross-sectional surface area of from 0.07 to 20 mm$^2$, and the cross-sectional shape may be circular, rectangular, oval, triangular or any other non-specific shapes. A part of the surface constituting this flow passage may be made of a material other than the amphoteric ion exchange membrane, for instance, a polymer material such as an acrylic resin, a polyethylene, a polypropylene, a polystyrene, a fluorinated-type resin, a polyvinyl chloride or nylon, a metal such as stainless steel, or glass. Further, if necessary, a suitable packing material may be packed in the flow passage formed by the amphoteric ion exchange membrane. It is desirable to use such a packing material particularly when the cross-sectional surface area of the flow passage formed by the amphoteric ion exchange membrane is 1 mm$^2$ or more. When the flow passage formed by the amphoteric ion exchange membrane is tubular, such a packing material may be spherical or substantially spherical particles or threads having a diameter of from 0.2 to 0.8 time the inner diameter of the tube, and when the flow passage formed by the amphoteric ion exchange membrane is of a shape other than the tubular shape, the packing material may be spherical or substantially spherical particles or threads having a diameter of from 0.2 to 0.8 time the maximum diameter of the cross section of the flow passage. The effects of the packing material include (1) that the solution in the flow passage is thereby mixed in a direction perpendicular to the membrane, whereby the diffusion rate of the electrolyte is improved, and (2) that the flow path is thereby narrowed down, whereby the spread of chromatogram bands can be avoided.

In the present invention, the low molecular weight electrolyte diffusable through the amphoteric ion exchange membrane is an inorganic or organic electrolyte having a molecular weight of at most 500 g/mol. If the molecular weight exceeds 500 g/mol, the electrolyte will be hardly diffusable through the ion exchange membrane even when ionized into ions. For better permeability, the molecular weight of the electrolyte is preferably at most 200 g/mol.

The concentration of the electrolyte contained in the column eluate (eluting solution) is preferably at most 2 mol/liter, more preferably at most 1 mol/liter. This column eluate may contain an organic non-electrolyte having a concentration of not higher than 50 g/dl. However, when the column eluate contains an organic non-electrolyte having a concentration of at least 5 g/dl, the hindrance to the diffusion of the electrolyte through the membrane is likely to increase due to the osmotic pressure difference. Therefore, in order to prevent a deterioration in the effects of the present invention, it is desirable to incorporate a non-electrolyte to the dialytic solution in a concentration at least equal to the molar concentration of the organic non-electrolyte.

Now, the apparatus of the present invention will be described in detail with reference to the accompanying drawings.

FIG. 1 is a diagram illustrating one embodiment of the present invention. A chromatographic column C is packed with particulate packing material or with a gel. A sample introduced together with an eluting solution from a column inlet 2, is separated here into its respective components, and discharged from a column outlet 5. This eluting solution (mobile phase) $L_1$ is sent from an eluting solution tank $T_1$ by a solution supply pump $P_1$ via a conduit 1 and, if necessary, a line filter F to a sample injection valve B having a sample injection inlet 3 and an outlet 4, and introduced into the column C together with a sample introduced from the sample injection inlet 3. The column eluate containing the fractionated sample is introduced into a flow passage of a dialyzer D, which flow passage is formed by an amphoteric ion exchange membrane M. On the other hand, a dialyzate solution $L_2$ is introduced by a pump $P_2$ from a tank $T_2$ to an inlet 6 of the dialyzer D, whereupon the removal of a low molecular weight electrolyte contained in the eluate or the exchange of such an electrolyte with an electrolyte contained in the dialytic solution, or the introduction of a necessary electrolyte into the eluate, is conducted through the amphoteric ion exchange membrane. Then, the eluate is sent to a detector S, and the dialyzate solution is discharged from an outlet 7. The chromatogram is detected by the detector S, and the respective fractions are passed through valve V to either outlet 8 or a fraction collector $F_c$. However, the final fraction collector is not required when the operation is intended for the analysis only. The dialyzer D employing the amphoteric ion exchange membrane M is preferably the one which has a built-in coiled tubular amphoteric ion exchange membrane.

In a case where the electrolyte in the solution does not interfere with the detection of the chromatogram and it is intended to separate and purify only a necessary component, it is advisable oo employ a liquid chromatography apparatus as shown in FIG. 2. FIG. 2 differs from FIG. 1 in that the eluate from the chromatographic column C is first sent to a detector S whereby the chromatogram is dectected, and then only the eluaee fraction containing the necessary component is sent to the dialyzer D, whereupon the low molecular weight electrolyte is removed and the necessary component is recovered by the fraction collector $F_c$. On the other hand, unnecessary eluate fractions are discharged from valve V throught outlet 8.

The packing material for the liquid chromatography colum is selected from a various types depending upon the object to be separated. For instance, the packing material includes silica gel, a porous polymer (gel) having polar groups such as hydroxy groups, cation exchange groups or anion exchange groups, and silica gel chemically bonded with octadecylsilane, octyl groups, phenyl groups, cyano groups, hydroxyl groups, amino groups, cation exchange groups or anion exchange groups. The liquid chromatography is classified based on the column separation mechanism into ion pair chromatography, absorption chromatography, affinity chromatography, partition chromatography, reversed phase chromatography, ion exchange chromatography, ion chromatography and gel permeation chromatography. The liquid chromatography in the present invention may be any one of these chromatographies.

Now, the present invention will be described in further detail with reference to Examples. However, it should be understood that the present invention is by no means restricted by these specific Examples.

EXAMPLE 1

A four component pentablock copolymer wherein polyisoprene (I), polybutadiene (B), polystyrene (S) and poly(4-vinylbenzyldimethylamine) (A) were linked in the order of I-S-B-A-I (wherein the S segment, the A segment, the I segment and the B segment were 27%, 34%, 20% and 19%, respectively, by weight, and the number average molecular weight of the entire copolymer was $2.1 \times 10^5$ g/mol), was dissolved n xylene, and the polymer concentration was adjusted to 18% by weight. Then, this solution was applied to a tubular net (opening rate: about 50%) having an outer diameter of 1 mm obtained by weaving a polyethylene yarn having a filament diameter of about 80 μm, and then slowly dried. Then, it was treated in a vapour of methyl iodide to quaternize the A segment, and then treated with a nitromethane solution containing 20% by volume of sulfur chloride to cross-link the I and B segments, and further treated with a dichloroethane solution containing 2% by volume of chlorosulfonic acid to sulfonate the S segment. The tubular membrane thus obtained, was washed with aqueous alkaline and acid solutions and with an aqueous sodium chloride solution, and then the cation and anion exchange capacities were measured by a usual method and found to be 0.80 meq and 0.69 meq, respectively, per 1 g of the dried membrane. Thus, it is evident that an amphoteric ion exchange membrane was obtained. This amphoteric ion exchange membrane was immersed in a 1 M lead acetate aqueous solution to dye the sulfonated S segment. Then, the membrane was sliced into a super thin fragment having a thickness of about 500 Å, which is then treated with a vapour of osmium tetroxide and observed by a transmission type electron microscope, whereby a lamellar structure wherein a black layer (sulfonated S segment, $S^-$), a white layer (cross-linked I and B segments, $\underline{D}$) and a gray layer (quaternized A semment, $A^+$) were arranged in a repeating unit of $-S^--\underline{D}-A^+-\underline{D}-$, was confirmed. The thickness of each layer was about 150 Å. The potential difference created between both sides of the amphoteric ion exchange membrane was measured by a usual method by means of a calomel electrode by passing 0.01 mol/liter of an aqueous KCl solution in the interior of the tubular amphoteric ion exchange membrane and 0.02 mol/liter of an aqueous KCl solution to the exterior of the membrane, whereby the electric potential was found to be +2.5 mV (as measured by using the exterior side of the membrane as the reference). Further, by using silver-silver chloride electrodes, the membrane resistance was measured in a 0.5 M KCl aqueous solution, whereby the membrane resistance was found to be 4.5 ohm.cm$^2$.

A Teflon thread having a diameter of 0.5 mm was inserted in the interior of the tubular amphoteric ion exchange membrane having a length of 2 m, and the tubular membrane was coiled to obtain a dialyzer. By using this dialyzer, a liquid chromatography apparatus as shown in FIG. 2 was assembled. Here, as the column C, two columns of gel permeation chromatography column G 3000SW (internal diameter: 7.5 mm, length: 60 cm, manufactured by Toyo Soda Manufacturing Co., Ltd.) were used in series, and as the detector, a ultraviolet absorption meter was used. The conditions for the chromatography were as follows.

Eluting solution: 0.1 M phosphate buffer solution (pH=7.0)/0.2 M KCl (1 ml/min).
Dialyzate solution: Pure water.
Sample: Bovine serum albumin (concentration: 0.1% by weight) (injected amount: 0.5 ml).

As the result, in the recovered fraction of an aqueous solution containing the albumin monomer, the concentration of each of phosphoric acid ions, chlorine ions and potassium ions, was 1/100 or less in the eluate. The recovery rate of albumin was about 90%, and the spread of the chromatogram peak (the increase of the half-value width) due to the dialyzer D was about 20%. Further, by using the aqueous solution fraction of the albumin monomer as recovered, the electrophoresis measurement by means of an argar gel was conducted by a usual method, whereby it was possible to conduct the measurement without any problems. Thus, it is evident that according to the present invention, the separation and purification of albumin can readily be conducted.

COMPARATIVE EXAMPLE 1

The separation of the bovine serum albumin was conducted in the same manner as in Example 1 except that the dialyzer provided with the amphoteric ion exchange membrane, was not used. The recovered aquoous solution fraction of the albumin monomer, contained substantial amounts of salts, and it was impossible to conduct the electrophoresis measurement by using the fraction as recovered. This aqueous solution fraction was subjected to desalination by means of an ion exchange gel, whereby albumin was recovered only 40%.

EXAMPLE 2

In Example 1, as the chromatographic column, phenyl-5 PW (internal diameter: 7.5 mm, length: 7.5 cm) manufactured by Toyo Soda Manufacturing Co., Ltd., was used, as the detector, an infrared absorption meter and an ultraviolet absorption meter were used in series, and as the eluting solution, A (1.7 M ammonium sulfate+0.1 M phosphate buffer solution pH=7.0) and B (0.1 M phosphate buffer solution pH=7.0) were used to give a linear gradient (60 minutes) from A to B. Other conditions were the same as those in Example 1, and the separation of a mixture comprising cytochrome C, myoglobin and lysozyme, was conducted. As the results, it was possible to detect the above-mentioned proteins at the absorption wave lengths thereof outside the region for the absorption wave length of water, and completely separated three chromatogram peaks were confirmed. Further, from the aqueous solutions containing the respective proteins, water was evaporated, and the infrared absorption spectra were measured, whereby the spectra were substantially the same as those of the respective pure proteins.

COMPARATIVE EXAMPLE 2

The separation of proteins were conducted in the same manner as in Example 2 except that the dialyzer provided with the amphoteric ion exchange membrane, was removed from the chromatography apparatus. From the recovered aqueous solutions containing the respective proteins, water was evaporated, and the infrared absorption spectra were measured, whereby due to the interference by the phosphoric acid salt and ammonium sulfate, it was impossible to obtain spectra for the proteins.

EXAMPLE 3

The separation of a mixture comprising saccharose, glucose and ructose, was conducted under the same conditions as in Example 1 except that in Example, the chromatographic column was changed to IEX-210SC (internal diameter: 7.5 mm, length: 60 cm) manufactured by Toyo Soda Manufacturing Co., Ltd. and having sulfonic acid groups, the detector was changed to a differential refractometer, and the eluting solution was changed to a 0.04 M sodium chloride aqueous solution. As the results, these three types of sacchaiides were substantially completely separated, and the concentrations of $Na^+$ and $Cl^-$ ions contained in the recovered solution, were not higher than 10 ppm.

EXAMPLE 4

In Example 1, the chromatographic column was changed to a column having an internal diameter of 7.5 mm and a length of 30 cm and packed with Protein A-Sepharose CL-4B (Pharmacia Fine Chemicals), and the separation of a mouse serum was conducted in the following manner.

(1) The column was washed with a 0.05 M phosphate buffer solution (which contains 0.15 M sodium chloride, pH=8.0) (solution C).

(2) The mouse serum was diluted twice and brought to a dialytic equilibrium state with solution C, and the sample thus adjusted was supplied from a sample loop at a rate of 0.2 ml/min, to have the iminological proteins adsorbed by the column.

(3) Solution C was supplied for washing.

(4) By using solution C and a 0.05 M citrate buffer solution (which contains 0.15 M sodium chloride, pH=3.5) (solution D), the elution of the immunological globulins ($I_gG_l$, $I_gG_{2a}$, $I_gG_{2b}$) was conducted by giving a linear gradient from solution C to solution D. Here, the flow rate of the eluting solution was 0.5 ml/min. In the dialyzer provided with the amphoteric ion exchange membrane, a dialyzate solution composed of a 0.01 M phosphate buffer solution (which contains 0.15 M sodium chloride, pH=7.2), was permitted to flow at a flow rate of 3 ml/min.

As the results, the immunological globulins $I_gG_l$, $I_gG_{2a}$ and $I_gG_{2b}$ were eluted at pH regions of from 6.0 to 7.0, from 4.5 to 5.0, and from 3.5 to 4.0, respectively. The pH of each eluate was about 7. The respective immunological globulins could be maintained in a stabilized condition thereafter without subjecting them to any special treatment like dialysis.

COMPARATIVE EXAMPLE 3

The separation of a mixture comprising saccharose, glucose and fructose, was conducted in the same manner as in Example 3 except that in Example 3, the amphoteric ion exchange membrane was changed to an experimental perfluorinated tube 811 x (internal diameter: 0.625 mm, outer diameter: 0.875 mm, length: 2 m) manufactured by DuPont Co. As the results, the saccharides could be separated substantially completely, but in the recovered solutions, sodium chloride was contained in a concentration substantially the same as the concentration in the initial eluting solution.

COMPARATIVE EXAMPLE 4

The separation of a mixture comprising saccharose, glucose and fructose, was conducted under the same conditions as in Example 3 except that in Example 3, the amphoteric ion exchange membrane was changed to hollow fibers (molecular weight for fractionation: 1000, catalogue No. 132215, number of fibers: 22) manufactured by Spectrum Co. As the results, the saccharides leaked through the membrane in substantial amounts, and the recovery rate was not higher than 10%.

As described in the foregoing, according to the present invention, a chromatographic column eluate is subjected to a dialytic treatment by means of an amphoteric ion exchange membrane, whereby the separation and purification of intermediate and low molecular weight organic substances in various biological substances, such as saccharides, oligopeptides, amino acids, nucleic acid substances, antibiotics, coenzymes, vitamins, organic acids, oligosaccharides or alcohols, and natural water-soluble polymers such as proteins, enzymes, nucleic acid or polysaccharides, or synthetic water-soluble polymers such as polyacrylic acid, polyethylene glycol, polystyrene sulfonic acid, polyamine and polypeptides, can be conducted quickly and highly efficiently. Further, liquid chromatography which used to be hardly employed for qualitative analysis, can now be employed extensively for qualitative analysis, since a substance isolated by the dialysis by means of the amphoteric ion exchange membrane, can now be readily analysed by a method such as a NMR method, an infrared absorption spectrum method, an electrochemical measurement, an electrophoresis method, an X-ray diffraction method, an elemental analysis, an ultraviolet absorption spectrum method or a mass spectrography. The present invention is effective particularly for the analysis of biochemical substances.

What is claimed is:

1. A method for analyzing a sample containing low and intermediate molecular weight components and separating the components by liquid column chromatography, which consists essentially of:
   (a) introducing a sample which contains low and intermediate molecular weight components and as eluting solution into a packed chromatography column to effect separation of the components in the sample;
   (b) passing an eluate from the column through a flow passage containing an amphoteric ion exchange membane, so as to subject said eluate to dialysis with a dialyzate solution to substantially remove electrolytes from the eluate; and
   (c) recovering the separated components and detecting said separated components either before or after said dialysis, wherein said amphoteric ion exchange membrane contains either cation and anion exchange, regions only or cation and anion exchange regions and regions having no ion exchange groups, said regions being positioned such that centers of adjacent regions are not more than about 1 mm apart, and wherein cation and anion exchange capacities of the amphoteric ion exchange membrane are, respectively, from about 0.1 to 2 meq/g of dry resin, and further werein said amphoteric ion exchange membrane has a potential difference of from $-8$ to $+8$ mV as measured between both sides of the membrane when one side of the membrane is in contact with 0.02 mol/liter of an aqueous potassium chloride solution and the other side is in contact with 0.01 mol/liter of an aqueous potassium chloride solution, and a membrane resistance of at most 50 ohm-cm$^2$ as measured in 0.5 mol/liter of an aqueous potassium chloride solution.

2. The method according to claim 1, wherein the amphoteric ion exchange membrane is a membrane containing only cation exchange regions and anion exhange regions.

3. The method according to claim 1, wherein the amphoteric ion exchange membrane is a membrane containing cation exchange regions, anion exchange regions and regions devoid of ion exchange groups.

4. The method according to claim 1, wherein the amphoteric ion exchange membrane is a membrane wherein cation exchange regions and anion exchange regions are alternately arranged.

5. The method according to claim 1, wherein the amphoteric ion exchange membrane is a membrane wherein cation exchange regions and anion exchange regions are adjacent to each other.

6. The method according to claim 1, wherein the dialyzate solution for the dialysis is an aqueous solution containing no non-electrolyte.

7. The method according to claim 1, wherein the dialyzate solution for the dialysis is an aqueous solution containing at most 50 g/dl of a non-electrolyte having a molecular weight of at least 10,000 g/mol.

8. The method according to claim 1, wherein the dialysis is conducted by permitting the eluate from the column to pass through the flow passage which is a tubular member made of the amphoteric ion exchange membrane having an internal diameter of from 0.3 to 5 mm.

9. The method according to claim 1, wherein the dialysis is conducted by permitting the eluate from the column to pass through the flow passage which is a tube made of the amphoteric ion exchange membrane and packed with a packing material.

10. The method according to claim 9, wherein the packing material is spherical or almost spherical particles or threads having a diameter of from 0.2 to 0.8 times the inner diameter of the tubular amphoteric ion exchange membrane.

11. The method according to claim 1, wherein the liquid chromatography is selected from the group oonsisting of ion pair chromatography, absorption chromatography, partition chromatography, affinity chromatography, reversed phase chromatography, ion-exchange chromatography, ion chromatography and gel permeation chromatography.

12. The method according to claim 1, wherein the amphoteric membrane has a potential difference of from $-4$ to $+4$ mV as measured between both sides of the membrance when one side of the membrane is in contact with 0.02 mol/liter of an aqueous potassium chloride solution and the other side is in contact with 0.01 mol/liter of an aqueous potassium chloride solution, and a membrane resistance of at most 20 ohm.cm$^2$ as measured in 0.5 mol/liter of an aqueous potassium chloride solution.

13. The method according to claim 1, wherein said eluate contains an organic non-electrolyte and the dialyzate solution contains a non-electrolyte in a concentration at least equal to the molar concentration of the organic non-electrolyte in the eluate.

14. The method according to claim 1, wherein said eluate contains an electrolyte which is an organic or inorganic electrolyte having a molecular weight of at most 500 g/mol.

15. The method according to claim 14, wherein said electrolyte has a molecular weight of at most 200 g/mol.

16. An apparatus for analyzing a sample containing low and intermediate molecular weight components and separating the components by liquid column chromatography, which consists essentially of:
   (a) a chromatographic column having an inlet and outlet for an eluting solution;
   (b) a flow passage connected to the outlet of said column, said flow passage having a dialyzer containing an amphoteric ion exchange membrane, and also having an inlet for a dialyzate solution; and
   (c) a fraction collector downstream of said dialyzer and a detector either upstream or downstream of the dialyzer; wherein said amphoteric ion exchange membrane contains either cation and anion exchange regions only or cation and anion exchange regions and regions having no ion exchange groups, said regions being positioned such that centers of adjacent regions are not more than about 1 mm apart, and wherein cation and anion exchange capacities of the amphoteric ion exchange membrane are, respectively from about 0.1 to 2 meq/g of dry resin, and further wherein said amphoteric ion exchange membrane has a potential difference of from $-8$ to $+8$ mV as measured between both sides of the membrane when one side of the membrane is in contact with 0.02 mol/liter of an aqueous potassium chloride solution and the other side is in contact with 0.01 mol/liter of an aqueous potassium chloride solution, and a membrane resistance of at most 50 ohm-cm$^2$ as measured in 0.5 mol/liter of an aqueous potassium chloride solution.

17. The apparatus according to claim 16, wherein the amphoteric ion exchange membrane containing dialyzer for a chromatographic eluate is disposed immediately after the chromatographic column.

18. The apparatus according to claim 16, wherein the amphoteric ion exchange membrane containing dialyzer for a chromatographic eluate is disposed after the detector.

19. The apparatus according to claim 16, wherein the dialyzer has a built-in coiled tubular member made from the amphoteric ion exchange membrane.

20. The apparatus according to claim 16, wherein the flow passage is formed by the amphoteric ion exchange membrane and has a cross-sectional surface area of 0.07 to 20 mm$^2$.

* * * * *